United States Patent [19]

Plum et al.

[11] Patent Number: 4,684,663

[45] Date of Patent: Aug. 4, 1987

[54] BIOCIDAL TRIBUTYLTIN COMPOUNDS

[75] Inventors: Hans Plum, Hamm; Horst Landsiedel, Froendenberg, both of Fed. Rep. of Germany

[73] Assignee: Schering Aktiengesellschaft, Berlin and Bergkamen, Fed. Rep. of Germany

[21] Appl. No.: 856,347

[22] Filed: Apr. 28, 1986

[30] Foreign Application Priority Data

May 9, 1985 [DE] Fed. Rep. of Germany ....... 3516695

[51] Int. Cl.$^4$ .......................... C07F 7/22; A01N 55/04; A61K 31/32
[52] U.S. Cl. ........................................ 514/493; 556/88
[58] Field of Search .......................... 556/88; 514/493

[56] References Cited

U.S. PATENT DOCUMENTS

| 2,583,419 | 1/1952 | Faulkner et al. | 556/88 |
| 2,745,820 | 5/1956 | Mack | 556/88 X |
| 3,219,697 | 11/1965 | Cox et al. | 556/88 X |
| 3,422,127 | 1/1969 | Fish | 260/429.7 |
| 3,781,316 | 12/1973 | Gitlitz | 556/88 X |
| 3,892,862 | 7/1975 | Gitlitz | 424/288 |

*Primary Examiner*—Helen M. S. Sneed
*Attorney, Agent, or Firm*—Curtis, Morris & Safford

[57] ABSTRACT

Tri-n-butylstannyloxy tricyclodecanes, their preparation, and biocidal agents containing the same as active ingredients.

5 Claims, No Drawings

BIOCIDAL TRIBUTYLTIN COMPOUNDS

The present invention relates to certain tri-n-butylstannyloxy tricyclodecanes, to their preparation, and to biocidal agents containing such compounds as the active ingredient thereof.

Tributyltin compounds, for example tributyltin oxide, but also tributyltin esters of carboxylic acids, possess high biocidal activity against fungi and bacteria. They are therefore used on a large scale as biocidally active ingredients in many materials and as preservatives or disinfectants. The biocidal activity of tributyltin compounds is not limited to microorganisms but extends also to certain marine organisms. In antifouling paints, these compounds therefore prevent harmful fouling of ship bottoms with barnacles, mollusks, or algae.

An important use for triorganotin compounds is the preservation of freshly felled timber or freshly installed structural lumber from attack by wood damaging fungi. Because of their great effectiveness and their broad spectrum of activity, tributyltin compounds are used on a large scale as fungicides in wood preservatives.

These organotin compounds are mainly solutions of tributyltin oxide or tributyltin esters of organic acids, such as tributyltin benzoate, linoleate, or naphthenate, in organic solvents. However, aqueous tributyltin formulations can also be prepared by using emulsifying agents. Tributyltin compounds are effective even in very low concentrations.

What usually determines the effectiveness of the various tributyltin compounds is their tin content. Now, since the tributyltin esters of long chain carboxylic acids have a lower tin content than does tributyltin oxide, such esters must be used in appropriately larger amounts to obtain the same effect.

So far as is known, the biocidal activity of such tributyltin ester compounds is not directly related to the nature of the carboxylic acid used.

The biocidal activity of wood preservatives can be expressed by so called limiting values, with the lower value representing the concentration at which fungal attack can still occur and the upper value representing the concentration at which an attack will no longer occur.

For example, the limiting values in conformity with DIN 51,176 applicable to a typical wood destroying fungus (Coniophora puteana) are 0.34/0.70 kg/m$^3$ for tributyltin oxide and are correspondingly higher, namely 0.92/1.3 kg/m$^3$, for tributyltin linoleate.

Of greater importance for the suitability for use of biocides as wood preservatives is their long term stability. The preservative should protect the wood treated with it for as long as possible against microbial attack. In principle, tributyltin compounds are quite stable substances which permit wood preservatives having long lasting activity to be produced. However, under certain conditions such as elevated temperature or under the action of specific wood constituents, they can break down to biologically less active organotin compounds, with butyl groups being split off.

An important factor affecting the stability of wood preservatives is the thermal stability of their active ingredients. Biocide-treated wood that is subject to weathering can heat up to over 70° C. when exposed to the sun's rays over an extended period of time.

It has now been found that products of reaction of tributyltin oxide (TBTO) or tributyltin halides with tricyclodecane alcohols possess very high thermal stability in wood treated therewith, this stability being substantially greater than that of the compounds tributyltin oxide (TBTO), tributyltin naphthenate (TBTN), or linoleate (TBTL) which up to now have been widely used in wood preservation.

The invention thus relates to tributyltin derivatives of tricyclodecane (TCD) alcohols of the general formula

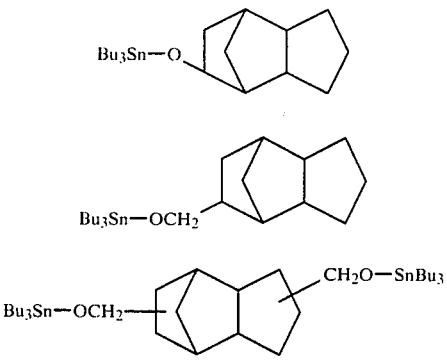

the compounds 8-tri-n-butylstannyloxytricyclo[5.2.1.0$^{2,6}$]decane, 8-tri-n-butylstannyloxymethyltricyclo[5.2.1.0$^{2,6}$]decane, and 3(4),8(9)-bis(tri-n-butylstannyloxymethyl)tricyclo[5.2.1.0$^{2,6}$]decane being preferred.

The invention further relates to a method for the preparation of such compounds wherein the appropriate TCD alcohol is reacted with bis-(tri-n-butyltin) oxide or with a tri-n-butyltin halide.

Moreover, the invention relates to a biocidal agent which contains as an active ingredient one or more of the aforesaid tributyltin compounds and is useful primarily for wood preservation.

The tricyclodecane alcohols to be used are known products which are marketed under the name "TCD alcohols" (Hoechst AG) and usually are obtained by appropriate reactions of the corresponding dicyclopentadiene. Thus, examples of suitable starting compounds for the tributyltin derivatives of the invention are:
8-hydroxytricyclo[5.2.1.0$^{2,6}$]decane,
8-hydroxymethyltricyclo[5.2.1.0$^{2,6}$]decane, and also
3(4),8(9)-bis(hydroxymethyl)tricyclo[5.2.1.0$^{2,6}$]decane.

By reaction of these alcohols with tributyltin oxide or a tributyltin halide, the compounds claimed in accordance with the invention can be prepared, for example,
8-tri-n-butylstannyloxytricyclo[5.2.1.0$^{2,6}$]decane (=TBT-TCD 1),
8-tri-n-butylstannyloxymethyltricyclo[5.2.1.0$^{2,6}$]decane (=TBT-TCD 2), and
3(4),8(9)-bis (tri-n-butylstannyloxymethyl)tricyclo[5.2.1.0$^{2,6}$]decane (=TBT-TCD 3).

Because of their excellent biocidal properties and their high stability, the compounds of the TBT-TCD series impart high, long lasting biocidal activity to materials treated therewith. They can therefore be used as active ingredients in wood and textile preservatives or in disinfectants, or also for the preservation of paints, adhesives, sealants, and drilling oils, and as active antifouling substances.

The compounds of the invention are used in the form of preparations such as solutions, emulsions, and dispersions, with or without binders and optionally with such additives as wetting, emulsifying, and dispersing agents, or are present in solid substrates or diluents.

The compounds of the invention can be applied to a substrate in the form of solutions, emulsions, or dispersions by spread coating, spraying, or impregnation, for example.

The concentration of active ingredients generally ranges from 0.05 to 50 percent and by weight of the formulation and is determined by the requirements of the use and by the absorptiveness of the substrate.

For the preservation of wood, solutions of the compounds of the invention in gasoline fractions, optionally with the addition of penetrating aids, binders, or other solvents, preferably have concentrations ranging from 0.05 to 5 percent by weight and are applied in amounts from 50 to 400 g of solution per square meter ($m^2$) of wood surface by spread coating, spraying, and the like.

Very effective wood preservation is achieved when the compounds of the invention, dissolved in an appropriate substance, are introduced into wood by special techniques such as the double vacuum method, the vacuum method, or the vacuum/pressure method, so that a loading of from 0.1 to 3.0, and preferably from 0.5 to 1.5, kg of active substance per cubic meter ($m^3$) of wood is obtained.

The compounds of the invention can also be used to prepare water dilutable formulations, which, too, are suitable for use in wood preservation, for example by spread coating, dipping, etc. with emulsions containing from 0.5 to 3 weight percent of active substance. For the protection of wood fiber products (e.g. pressboard, chip-board, etc.), the compounds of the invention may be added to a bonding agent or adhesive while in the form of a highly concentrated solution or a formulation with an emulsifier in amounts which provide from 0.1 to 2 percent by weight of the active substance.

For the protection of materials such as cotton fabrics against undesired microorganisms, the compounds of the invention may be applied by spraying or impregnation using solutions, for example in ethanol, xylene or a ketone, with concentrations of the active ingredient ranging from 0.05 to 3 percent by weight, optionally with the addition of hydrophobizing agents.

To broaden the spectrum of their activity, to obtain special activity against specific microorganisms, or to impart insecticidal properties thereto, the compounds of the invention may be combined with other active substances. Suitable for this purpose are, for example:
3-iodo-2-propynylbutyl carbamate;
copper naphthenate;
copper 8-hydroxyquinoline;
N-cyclohexyl-N-methoxy-2,5-dimethylfuran-3-carboxylamide;
N,N'-dimethyl-N'-phenyl-N'-fluorodichloromethylthiosulfonyldiamide;
benzimidazole-2-carbamic acid methyl ester;
N-(trichloromethylthio)phthalimide;
gamma-hexachlorocyclohexane; and
"Permethrin", i.e. 3-phenoxybenzyl(1R,1RS)-cis,trans3-(2,2-dichlorovinyl)-2,2-dimethylcyclopropane-1-carboxylate.

A better understanding of the present invention and of its many advantages will be and by referring to the following specific examples, given by way of illustration.

EXAMPLE 1

One mole of 8-hydroxytricyclo[5.2.1.0$^{2,6}$]decane and one-half mole of tributyltin oxide were heated with about 1200 ml of xylene to reflux with stirring. Over about 3 hours, the water of reaction formed was quantitatively eliminated by azeotropic distillation. The solvent was then distilled off.

A pale yellow liquid product having a tin content of 26.5% was obtained as a residue which readily dissolves in organic solvents such as alcohols, ketones, chlorinated hydrocarbons, and gasolines. However, it is difficultly soluble in water.

EXAMPLE 2

One mole of 8-hydroxymethyltricyclo[5.2.1.0$^{2,6}$]decane and one-half mole of tributyltin oxide were heated with about 1200 ml of xylene to reflux with stirring. Over about 3 hours, the water of reaction formed was quantitatively eliminated by azeotropic distillation. The solvent was then distilled off.

A yellow liquid having a tin content of 25.4% was obtained as a residue which readily dissolves in organic solvents such as alcohols, ketones, chlorinated hydrocarbons, and gasolines. However, it is difficultly soluble in water.

EXAMPLE 3

One mole of 3(4),8(9)-bis(hydroxymethyl)tricyclo[5.2.1.0$^{2,6}$]decane and one mole of tributyltin oxide were heated with about 1500 ml of xylene to reflux with stirring. Over about 3 hours, the water of reaction formed was quantitatively eliminated by azeotropic distillation. The solvent was then distilled off.

A liquid product of pale yellow color having a tin content of 30.4% was obtained as a residue which readily dissolves in organic solvents such as alcohols, ketones, chlorinated hydrocarbons, and gasolines. However, it is only sparingly soluble in water.

EXAMPLE 4

One mole of 3(4),8(9)-bis(hydroxymethyl)tricyclo[5.2.1.0$^{2,6}$]decane was warmed to about 50° C. with 1 mole of tri-n-butyltin chloride, with stirring. One mole of solid sodium hydride was added portionwise and the temperature was raised to about 100° C. and the mixture was maintained at this temperature for about 1 hour with stirring. Precipitated NaCl was removed by filtration and the filtrate was washed with four 500 ml portions of water in a separating funnel. After drying over anhydrous sodium sulfate, a liquid product was obtained having the same properties as the product of Example 3.

Analysis of Stability in Wood

The long term stability of biocidal wood preservatives (Table I) can be determined by storage tests. To this end, blocks of pine sapwood measuring 5.0×2.5×1.5 cm were impregnated with solutions of the biocides to be tested and, after evaporation of the solvent, were stored for 4 weeks at 20° C. and then for 2 weeks at 80° C.

Then the wood blocks were chopped and extracted for 24 hours with an ethanol/HCl solution (0.3% HCl).

In the extracts, both the total tin and the tributyltin contents were determined. The results are reported in following Table I.

TABLE I

BREAKDOWN OF TRIBUTYLTIN COMPOUNDS IN WOOD

| Impregnating solution | Amount of Sn taken up | TBT content of starting substances | Extract Total tin content | TBT content of extracts |
|---|---|---|---|---|
| TBTO | 28.0 mg | 97.0% | 26.9 mg | 40.0% |
| TBTN | 27.0 mg | 95.0% | 24.7 mg | 47.0% |
| TBTL | 28.5 mg | 98.0% | 27.7 mg | 48.0% |
| TBT-TCD 1 | 27.5 mg | 98.0% | 26.0 mg | 75.0% |
| TBT-TCD 2 | 28.3 mg | 98.5% | 27.0 mg | 76.0% |
| TBT-TCD 3 | 29.0 mg | 98.0% | 26.5 mg | 78.0% |

While the tributyltin compounds TBTO, TBTN, and TBTL exhibit a reduction of the tributyltin content from 40 to 48 percent due to the stresses imposed by the extended testing, the reduction is substantially less in the case of the TBT-TCD compounds of the invention. Over 75 percent of tributyltin compound has been retained at the end of the storage test.

Biocidal Activity

The TBT-TCD compounds of the invention exhibit high biocidal activity against many bacteria and fungi. To determine their biocidal activity as reported in following Table II, filter paper disks having a diameter of 5.5 cm are impregnated with graded concentrations of the tributyltin compound in ethanol and, after drying, are tested against fungi and bacteria in an agar overlay test. The size of the zones of inhibition (width of growth free zone in mm) is used as a measure of the biocidal activity.

TABLE II

BIOCIDAL ACTIVITY OF TRIBUTYLTIN COMPOUNDS
(Agar Overlay Test-
Zones of inhibition around the specimens in mm)

| Active ingredient | Wt. % in impregnating solution* | Bacillus subtilis | Bacillus mesent. | Proteus vulgaris | Poria mont. | Cladosp. herbarum | Aureobas. pullulans | Trichoderma viride |
|---|---|---|---|---|---|---|---|---|
| TBTO | 0.5 | 2–3 | 3–4 | 0–1 | 5–7 | 3–4 | 1–2 | 0–1 |
|  | 1.0 | 5–2 | 5–6 | 2–3 | 8–10 | 6–8 | 3–4 | 2–3 |
|  | 3.0 | 10–12 | 10–12 | 4–5 | 12–15 | 8–10 | 5–6 | 4–6 |
| TBTN | 1.0 | 1–2 | 2–3 | 0 | 3–4 | 1–2 | 0–1 | 0 |
|  | 2.0 | 3–4 | 3–4 | 1–2 | 5–7 | 4–5 | 1–2 | 0–1 |
|  | 3.0 | 5–7 | 8–10 | 2–3 | 8–10 | 6–8 | 2–3 | 2–3 |
| TBT-TCD 1 | 0.75 | 1–2 | 2–3 | 0–1 | 2–4 | 2–3 | 0 | 0–1 |
|  | 1.5 | 3–4 | 3–4 | 1–2 | 4–6 | 3–4 | 0–2 | 1–2 |
|  | 2.25 | 6–8 | 6–7 | 3–4 | 7–8 | 5–7 | 2–3 | 3–4 |
| TBT-TCD 2 | 0.75 | 2–3 | 2–3 | 0–1 | 3–4 | 2–3 | 0–1 | 1–2 |
|  | 1.5 | 4–5 | 4–5 | 1–2 | 5–7 | 3–4 | 1–2 | 2–3 |
|  | 2.25 | 7–8 | 6–8 | 2–3 | 8–9 | 5–6 | 2–3 | 3–4 |
| TBT-TCD 3 | 0.75 | 2–3 | 2–3 | 0–1 | 4–5 | 2–3 | 0–1 | 0–1 |
|  | 1.5 | 5–6 | 4–5 | 1–2 | 6–8 | 4–6 | 1–2 | 1–2 |
|  | 2.25 | 8–10 | 8–10 | 3–4 | 8–10 | 6–8 | 3–4 | 3–4 |
| None | — | 0 | 0 | 0 | 0 | 0 | 0 | 0 |

*Concentrations corresponding to TBT contents

EXAMPLE 5

A colorless wood preserving primer containing little binder and comprising
2.0 pbw* of the reaction product of Example 3,
0.2 pbw of "Permethrin" (cis:trans=25:75),
6 pbw of diethylene glycol monobutyl ether,
8 pbw of long-oil alkyd resin (approx. 33% of phthalic resin and 67% of triglycerides of vegetable fatty acids), and
83.8 pbw of petroleum spirits
*) Parts by weight exhibits good penetrating capacity and lends itself readily to use as a wood preserving primer for structural timber.

EXAMPLE 6

A colored wood preserving glaze comprising
2.5 pbw of the reaction product of Example 3,
40 pbw of long-oil alkyd resin (see Example 1),
0.5 pbw of desiccants (Co, Mn, Pb salts),
0.5 pbw of an antisettling agent,
9.2 pbw of red iron oxide paste,
0.8 pbw of black iron oxide paste,
6 pbw of diethylene glycol monobutyl ether, and
39.3 pbw of petroleum spirits
is suitable for the surface coating of dimensionally stable structural wood parts such as window frames, doors, etc.

Example 7

A water dilutable combination of
15 pbw of the reaction product of Example 1,
5 pbw of N,N'-dimethyl-N'-fluorodichloromethylthiosulfonyldiamide, and
80 pbw of nonionic emulsifier
can be diluted over a wide range (1:5 to 1:50) with water and gives stable emulsions for the spread coating, spraying, or dipping of freshly felled timber, for example. The undiluted formulation is used in concentrations from 0.2 to 3 percent by weight to impart biocidal properties to aqueous coating systems, for example, dispersions of an acrylate resin, e.g. suitable for painting.

EXAMPLE 8

An solution for imparting biocidal properties to textiles, for example cotton canvas, comprising
3.0 pbw of the reaction product of Example 2,
3.6 pbw of micronized polyethylene wax, and
93.4 pbw of low-odor synthetic isoparaffin
can be applied either by spraying the solution onto the textile or by dipping the material to be treated.

EXAMPLE 9

An antifouling paint comprises
13 pbw of the reaction product of Example 1,
15 pbw of chlorinated rubber,
7 pbw of chlorinated paraffin (54% Cl), 40 pbw of rutile TiO$_2$ pigment, and 25 pbw of xylene.

In a stationary fouling test, this coating has so far remained free of fouling for two years.

What is claimed is:

1. A tri-n-butylstannyloxy tricyclodecane of the formula

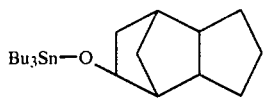

-continued

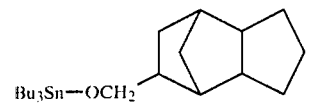

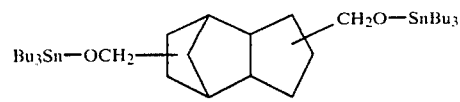

wherein Bu is n-butyl.

2. A compound as in claim 1 which is 8-tri-n-butylstannyloxytricyclo[5.2.1.0$^{2,6}$]decane.

3. A compound as in claim 1 which is 8-tri-n-butylstannyloxymethyltricyclo[5.2.1.0 $^{2,6}$]decane.

4. A compound as in claim 1 which is 3(4),8(9)-bis(tri-n-butylstannyloxymethyl)tricyclo[5.2.1.0$^{2,6}$]decane.

5. A biocidal agent comprising a biocidally effective amount of a compound as in claim 1 together with an inert carrier therefor.

* * * * *